United States Patent [19]

McIntyre

[11] Patent Number: 4,727,860

[45] Date of Patent: Mar. 1, 1988

[54] EXERCISE APPARATUS FOR THE KNEE

[75] Inventor: Donald R. McIntyre, Chapel Hill, N.C.

[73] Assignee: Isotechnologies, Inc., Hillsborough, N.C.

[21] Appl. No.: 871,514

[22] Filed: Jun. 6, 1986

[51] Int. Cl.⁴ .............................................. A61H 1/02
[52] U.S. Cl. .................................. 128/25 R; 272/130; 272/134; 272/96
[58] Field of Search .................. 128/25 R, 25 B, 782; 272/96, 130, 134, 70

[56] References Cited

U.S. PATENT DOCUMENTS

| | | | |
|---|---|---|---|
| T100,602 | 5/1981 | Roley et al. | 128/782 |
| 675,678 | 6/1901 | Scholder | 128/25 R |
| 3,103,357 | 9/1963 | Berne | |
| 3,702,138 | 11/1972 | Phillips et al. | |
| 3,784,194 | 1/1974 | Perrine | |
| 4,235,437 | 11/1980 | Ruis et al. | |
| 4,452,447 | 6/1984 | Lepley et al. | |
| 4,463,947 | 8/1984 | Kloenne | |
| 4,605,220 | 8/1986 | Troxel | 272/96 |
| 4,650,183 | 3/1987 | McIntyre | 272/96 |

FOREIGN PATENT DOCUMENTS

| | | | |
|---|---|---|---|
| 2535209 | 4/1984 | France | |
| WO80/00308 | 3/1980 | World Int. Prop. O. | |
| WO82/02668 | 8/1982 | World Int. Prop. O. | |
| 446148 | 3/1968 | Switzerland | |
| 113030 | 2/1918 | United Kingdom | 128/25 R |
| 1303395 | 6/1971 | United Kingdom | |
| 2112653 | 7/1983 | United Kingdom | |

OTHER PUBLICATIONS

"The LIDO 2.0 Rehabilitation System" by Loredan Biomedical.
Cybex advertisement entitled "Two of the . . . Cybex Testing and Rehabilitation".
"The Future of Muscle/Joint Therapy & Rehabilitation is Here" by Biodex Corporation, 1986, 6 pages.
"The Omni-Tron System I" by Hydra-Fitness Industries, advertisement.
Chattecx Corporation advertisement for the KINCOM Systems.
"The Biokinetic Modular Therapy System" by Biokinetic Fitness Laboratories, Inc.
"Genucom Complete Knee Evaluation" by Far Orthopedics, Inc.
"Johnson Anti-Shear Accessory" by Cybex Corporation.
"Orthotron KT 1 & KT 2" by Cybex Corporation.
"Isolated-Joint Testing & Exercise" A handbook for using Cybex II and the U.B.X.T. by Cybex Corporation.

*Primary Examiner*—Richard J. Apley
*Assistant Examiner*—J. Welsh
*Attorney, Agent, or Firm*—Richard E. Jenkins

[57] ABSTRACT

A knee exercise apparatus which provides for movement about three axes which correspond to and are coaxial with the knee joint axes of flexion/extension, tibial rotation and abduction/adduction. A specific arrangement for independently measuring torque and concomitant angular position changes about the knee joint axis of flexion/extension and tibial rotation as well as angular position changes about the axis of abduction/adduction is shown and described as are associated restraints to minimize superfluous movement about joints adjacent to the knee joint of interest.

10 Claims, 5 Drawing Figures

EXERCISE APPARATUS FOR THE KNEE

DESCRIPTION

1. Technical Field

This invention relates to an exercise apparatus for the knee, and more particularly to apparatus of the type operable by human user movements against predetermined resistance. The apparatus of the invention has been specifically designed to measure the functional characteristics of the knee joint and provides for accurate measurement of the torques and the concomitant angular position changes about the flexion/extension and tibial rotation knee joint axes. In addition, accurate measurement may be made of angular position change about the axis of abduction and adduction.

2. Background Art

The use of an exercise apparatus in order to exercise for physical therapy purposes or to exercise in order to facilitate diagnostic and rehabilitation is known. Moreover, it has recently become known to electrically connect a suitably programmed personal computer to exercise apparatus in order to better determine the functional characteristics of certain natural joints such as the knee and ankle. Representative knee exercise apparatus would probably include the CYBEX II apparatus manufactured by Lumex, Inc. of Ronkonkoma, N.Y., the KIN-KOM machine manufactured by Chattecx Corporation of Chattanooga, Tenn., the LIDO apparatus manufactured by Loredan Biomedical, Inc. of Roswell, Ga. and the BIODEX machine manufactured by Biodex Corporation of Center Moriches, N.Y. Also of interest is the ORTHOTRON II apparatus manufactured also by Lumex, Inc. of Ronkonkoma, N.Y. It is believed by applicant that all of the aforementioned machines are constructed so as only to be able to evaluate knee movement about a singular axis at any given time. The apparatus of the invention is believed to be unique in its ability to simultaneously evaluate multi-axial movement of the knee of a user.

Commonly assigned U.S. Pat. No. 4,452,447 directed to an ankle exerciser apparatus may be of interest since it provides for movement about three mutually perpendicular axes against double-action hydraulic cylinders. However, it should be noted that this particular ankle exercise apparatus was found to result in binding of the ankle joint during exercise since the three mutually perpendicular axes of movement were not coaxial with the natural axes of the foot being evaluated. The result was an apparatus which was not entirely satisfactory with respect to its intended purpose. Also of possible interest are the exercise apparatus disclosed in Elmeskog PCT Publication No. WO 80/00308, Ruis et al. U.S. Pat. No. 4,235,437, Berne U.S. Pat. No. 3,103,357 and commonly assigned pending patent application Ser. No. 735,866 filed May 20, 1985 on "Exercise Apparatus for Certain Foot and Ankle Joints".

DISCLOSURE OF THE INVENTION

In accordance with the present invention, applicant provides a new knee exercise apparatus designed to measure the functional characteristics of the knee joint. Accurate measurement of the pounds-feet of torque exerted by pivotal movement about the flexion/extension and tibial rotation axes of the knee and the concomitant angular position changes as well as measurement of angular position changes during pivotal movement about the abduction/adduction axis of the knee are achieved by restricting motion both above and below the knee with suitable restraints and by aligning the axes of the knee so as to be substantially coaxial with the pivotal axes of movement provided for by the knee exercise apparatus. The instant invention is of a novel construction so as to accommodate tri-axial movement of the knee about the natural knee joint axes of flexion/extension, tibial rotation and abduction/adduction. A predetermined and independent resistance to movement can be selected for the axis of flexion/extension and the axis of tibial rotation movement of the knee. The knee may also be moved about the axis of abduction/adduction, but it is a free movement which is not against a resistance. Angular position changes may be measured simultaneously or for preselected individual movement about any of the three aforementioned axes of natural knee movement.

Therefore, it is a primary object of the present invention to improve the accuracy and precision by which the functional characteristics of knee joint performance are measured. In realizing this object of the present invention, exercise apparatus having means for measuring functional characteristics of movement about a singular knee joint axis at a point in time are improved by the provision of an apparatus having the ability to measure either simultaneously or selectively knee joint movement about all three natural axes of pivotal movement.

Yet a further object of the present invention is to provide a new apparatus of novel construction which is capable of monitoring the torques and concomitant angular position changes associated with knee movement about the axes of flexion/extension and tibial rotation.

Another object of the present invention is to provide a new apparatus of novel construction which can measure angular position change during movement about the abduction/adduction axis of the knee.

A still further object of the present invention is to provide a knee exercise apparatus adapted for pivotal movement about three axes which correspond to and are coaxial with the natural axes of knee joint flexion/extension, tibial rotation and abduction/adduction movement.

BRIEF DESCRIPTION OF THE DRAWINGS

Some of the objects of the invention having been stated, other objects will appear as the description proceeds, when taken in connection with the accompanying drawings, in which.

BEST MODE FOR CARRYING OUT THE INVENTION

While the present invention will be described hereinafter with particular reference to the accompanying drawings, in which a certain operating embodiment of the apparatus of the present invention is shown, it is to be understood at the outset of the description which follows that it is contemplated that apparatus in accordance with the present invention may be varied from the specific form described hereinafter, while still attaining the desired result of this invention. Accordingly, the description which follows is to be understood as a broad teaching disclosure directed to persons of appropriate skill in the appropriate arts, and not as limiting upon the scope of this invention.

Figures 1, 1A:
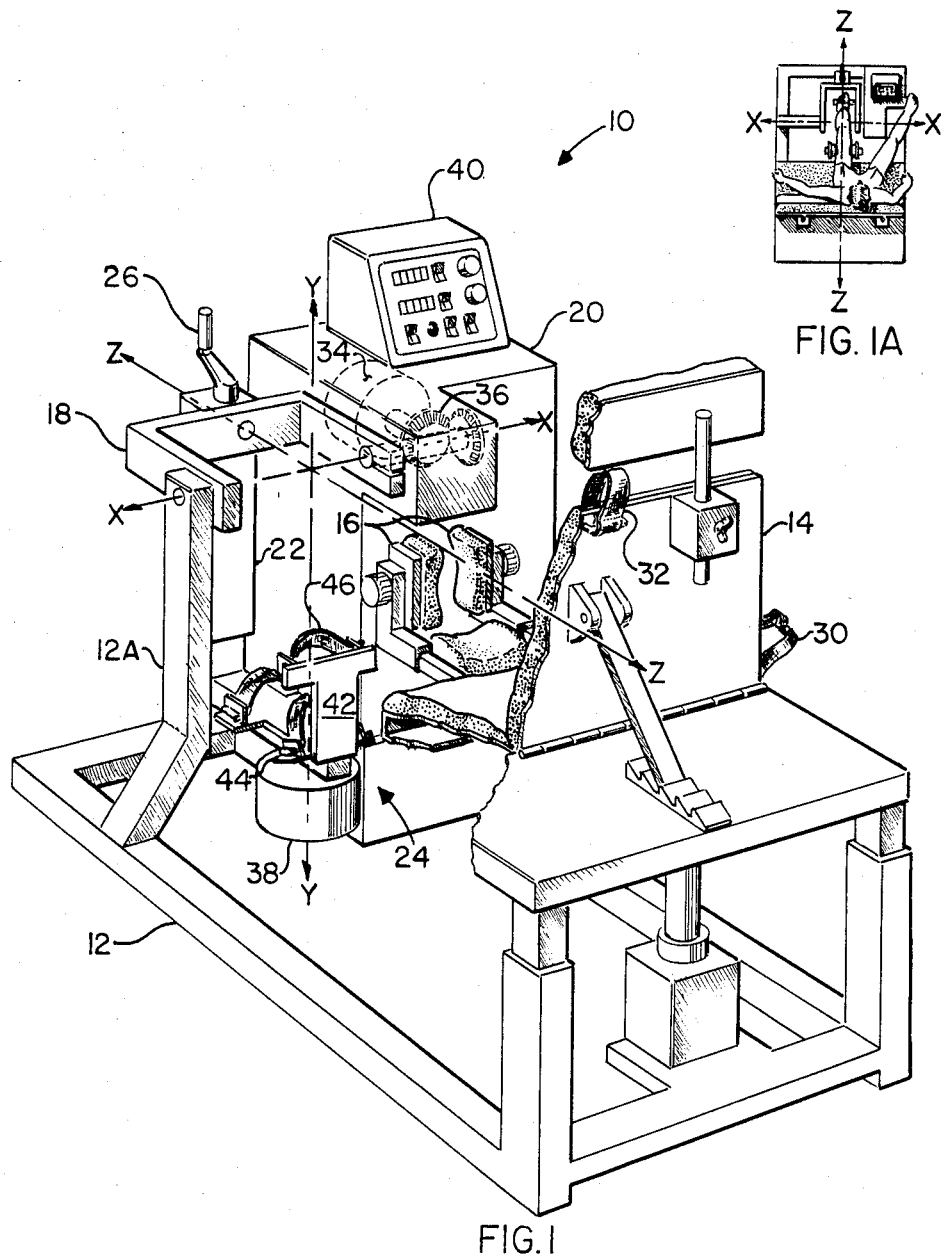
FIG. 1 is a perspective view of a knee exercise apparatus embodying the present invention.
FIG. 1A is a reduced size top view of the exercise apparatus of FIG. 1 with a user positioned thereon.
Figure 2:
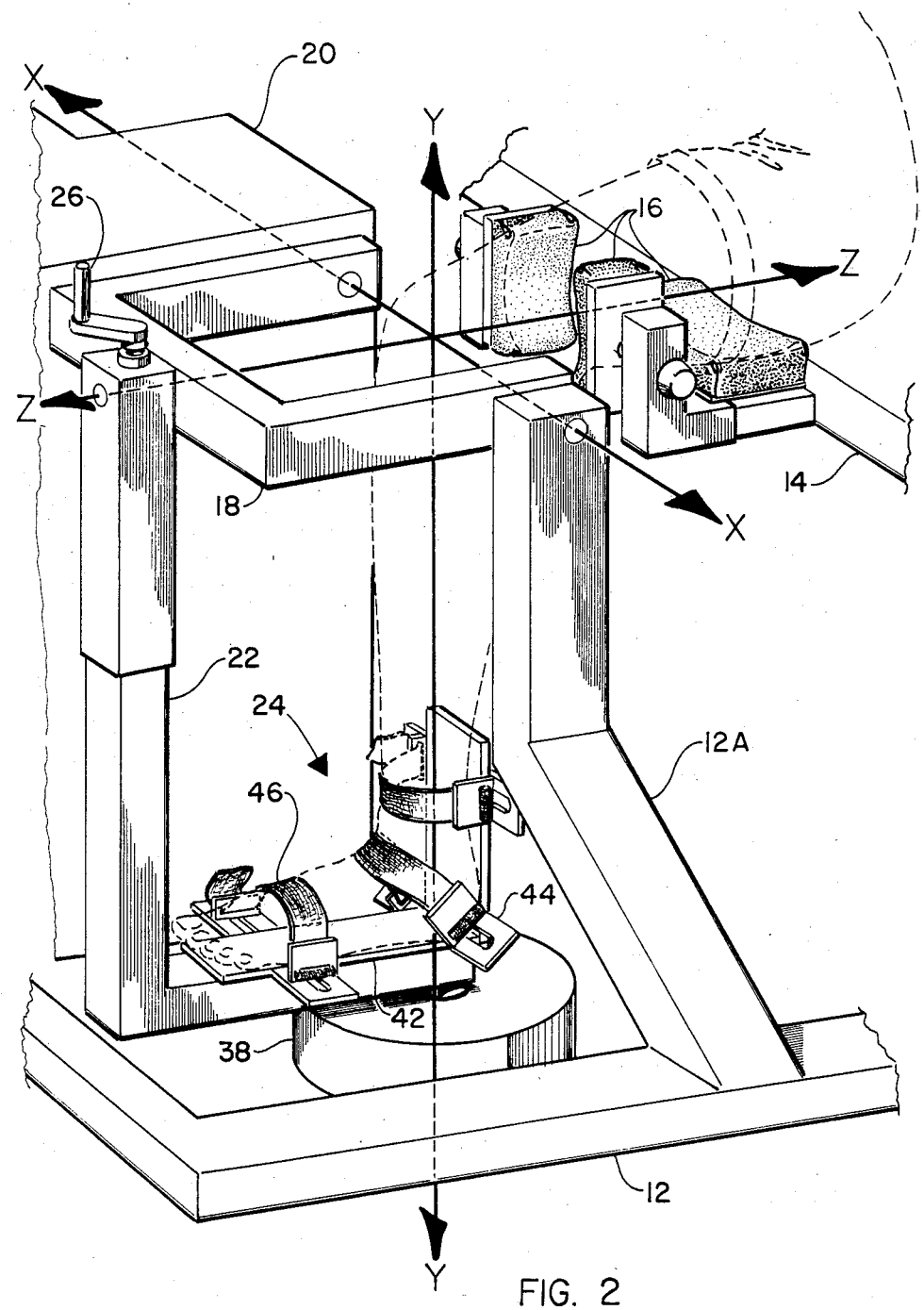
FIG. 2 is a perspective view of the knee movement assembly of the knee exercise apparatus with phantom lines depicting the leg of a user properly positioned thereon for clarity of understanding.
Figure 3:
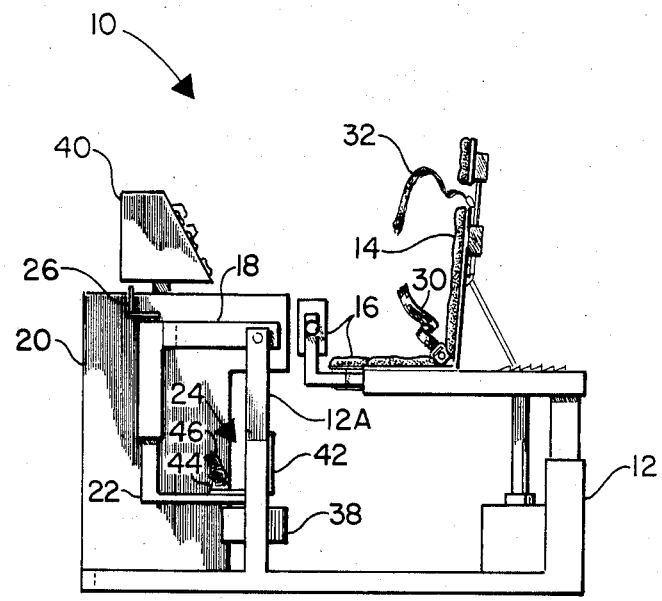
FIG. 3 is a side elevation view of the knee exercise apparatus of FIG. 1.

Referring now to FIGS. 1 through 3, a knee exercise apparatus embodying the present invention is there illustrated in the form of a knee exercise apparatus generally indicated at 10. In the form illustrated, apparatus 10 comprises a frame 12 which supports a seat 14 for a user and a thigh restraint 16 which is slidably secured to seat 14. A U-shaped gimbal 18 is pivotably mounted to upright frame member 12a at one end and at the other end to cabinet 20 which houses the hydraulic and electrical circuitry (not shown) of the apparatus. An L-shaped gimbal 22 is pivotably secured at its tip end to gimbal 18 and at its bottom end supportingly carries foot restraint 24. L-shaped gimbal 22 is provided with vertical adjustment 26 which comprises a conventional worm screw mechanism for adjusting the length of gimbal 22 relative to gimbal 18 in order to accommodate varying leg lengths of different users.

Seat 14 may be vertically and horizontally adjusted by means of a conventional electrical motor and gear assembly (not shown). The capability to adjust seat 14 up and down, forward and back is necessary in order for apparatus 10 to accommodate different body sizes and to facilitate correct alignment of the knee for proper measurement of the functional characteristics thereof. The back of seat 14 may also be inclined to modify the contribution of the knee exercise muscles which cross both the hip and knee joint of a user. Seat 14 is of relatively minimal depth and thus knee exercise has little effect on exercising of the hamstring muscle group. A hip restraint 30 and a trunk restraint 32 are adjustably secured to seat 14 in order to restrict both hip and trunk movement during knee performance evaluation. Thigh restraint 16 is slidably secured to seat 14 as noted above, and serves to both prevent extension of the thigh and to prohibit abduction/adduction about the hip joint in order to facilitate better evaluation of knee joint performance.

With reference again to U-shaped gimbal 18 and L-shaped gimbal 22, it should be appreciated that with a user correctly positioned on apparatus 10 and secured to thigh restraint 16 and foot restraint 24, U-shaped gimbal 18 pivots about an axis X (see FIG. 2) which is coaxial with the flexion/extension axis of knee movement. A hydraulic dynamometer 34 is operatively connected through gears 36 to U-shaped gimbal 18 to provide selected resistance to user knee movement about the axis of flexion/extension. A second dynamometer 38 is secured to the lower end of L-shaped gimbal 22 and foot restraint 24 is fixedly secured directly to the rotational shaft of dynamometer 38. Foot restraint 24 is positioned so as to pivot about an axis Y which is coaxial with the axis of tibial rotation of the knee of a user of apparatus 10. Dynanometer 38 therefore serves to provide a predetermined and selective resistance to movement of a user's knee about the axis of tibial rotation which is indeendent of the predetermined resistance provided by dynanometer 34 to movement about the X axis. As noted hereinabove, L-shaped gimbal 22 is pivotably attached at its top end to U-shaped gimbal 18. This axis of pivotal movement is designated Z in FIG. 2 and is coaxial with the abduction/adduction axis of knee movement. A resistance dynanometer is not provided in association with movement about axis Z.

Angular movement about each of axes X, Y and Z is measured with potentiometers (not shown). Control cabinet 20 contains control means for independently selecting the resistance to movement about the axis of flexion/extension and the axis of tibial rotation.

Figure 4:
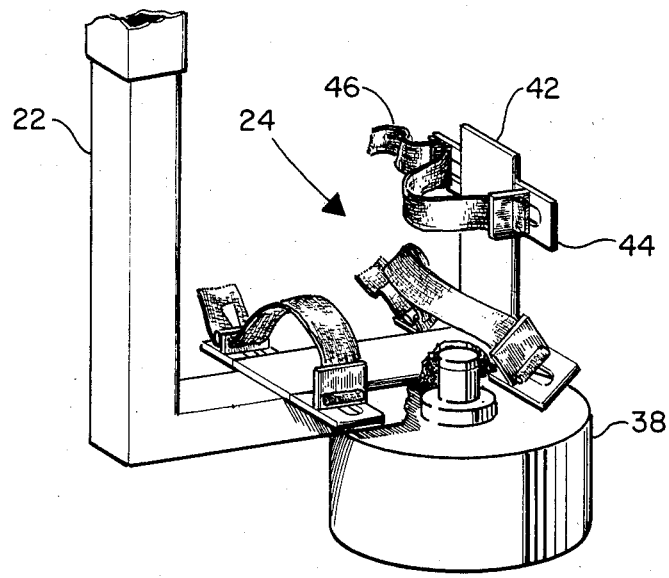
FIG. 4 is an enlarged perspective view of the foot restraint and associated gimbal and dynamometer of the knee exercise apparatus with parts broken away for clarity.

With reference now to FIG. 4, a better appreciation may be had of foot restraint 24. As can be seen, foot restraint 24 comprises an L-shaped foot plate 42 and six buckle-type strap attachments 44 to secure the foot of a user to foot restraint 24. Three strap attachments 44 are positioned on each side of foot plate 42 and adapted for in-out adjustment to accommodate different foot sizes. The location of strap attachments 44 is just above the ankle joint, at the midfoot and at the forefoot. Straps 46 serve to pass over the foot of the user and restrain the foot to foot plate 42. In this fashion, foot restraint 24 serves to restrict movement of the ankle and foot joints in order to transmit the torques and movements occuring during flexion/extension and tibial rotation knee movements and to further serve to transmit any medial and lateral collateral ligament laxity associated movement (abduction/adduction).

In operation, knee exercise apparatus 10 requires that a user be seated upon seat 14 of exercise apparatus 10. Next, the leg and the ankle joint of interest are initially positioned in thigh restraint 16 and foot restraint 24. It should be fully appreciated that either the right or left knee of a user may be evaluated on the apparatus of the instant invention. After the user is tentatively positioned on exercise apparatus 10, seat 14 and vertical adjustment 26 of gimbal 22 are carefully adjusted so that the user's knee joint axes of flexion/extension, tibial rotation and abduction/adduction correspond to the X, y and Z axes of movement of apparatus 10 and are, in fact, substantially coaxial therewith. Additionally, hip restraint 30, trunk restraint 32, thigh restraint 16 and foot plate straps 46 are adjusted to minimize superfluous movement about joints adjacent to the knee joint. The coaxial relationship of the three axes of movement of apparatus 10 and the knee joint of a user allow for the accurate measurement of functional characteristics of the knee joint. More specifically and as noted hereinbefore, apparatus 10 is adapted to measure torques and angular position changes about the knee joint axes of flexion/extension and tibial rotation and angular position changes about the axis of abduction/adduction. To accomplish the latter, the knee of a user is typically positioned in a near-extended posture with the thigh immobilized and L-shaped gimbal 22 is then manually pivoted by a physician or technician to the perceived limits of abduction/adduction movement. The angle changes may be subsequently equated to medial/lateral collateral ligament laxity for purposes of knee joint evaluation.

Although not shown, a suitably programmed and electrically connected personal computer may be utilized in order to analyze and record the pounds-feet of torque effort and the concomitant angular position changes during movement of the knee of a user about the X axis of flexion/extension and the Y axis of tibial rotation and the angular position changes about the Z axis of abduction/adduction in order to better determine functional characteristics of the knee joint. The computerized evaluation of knee joint movement may be utilized to determine the extent of deficiency of performance of the knee joint due to athletic injury or other causes such as aging or disease. It should also be appreciated that the computer program could be suitably utilized to provide graphs, reports and protocols in addition to storage/retrieval and comparisons.

In conclusion, the subject invention provides for a novel tri-axial knee excercise apparatus which is capable of heretofore unavailable performance evaluation accuracy in view of its ability to simultaneously accommodate and evaluate multi-axial knee movement. Applicant believes that the instant invention is novel and superior to any known knee exercise performance evaluation apparatus.

In the drawings and specification, there has been set forth a preferred embodiment of the invention, and although specific terms are employed, they are used in a generic and descriptive sense only and not for purposes of limitation.

What is claimed is:

1. An apparatus for exercising the knee of a user and comprising:
   a stationary frame:
   a knee exercise assembly pivotably mounted to said frame and including a pivotably movable support member and means depending downwardly therefrom for securing a foot of a user said support member being pivotably movable relative to said frame about a horizontal axis which corresponds to an axis of rotation which is coaxial with the axis of flexion/extension movement of the knee, and said means for securing the foot being pivotably movable relative to said support member about an axis of rotation which is generally perpendicular to said horizontal axis and coaxial with the axis of tibial rotation movement of the knee so as to permit simultaneous multi-axial pivotal movement of the knee about its natural axes;
   first resistance means operatively connected to and cooperating with said support member of said knee exercise assembly for resisting flexion/extension movement of the knee of a user;
   second resistance means, which can act simultaneously with said first resistance means, operatively connected to and cooperating with said foot securement means of said knee exercise assembly for resisting tibial rotation movement of the knee of a user; and
   restraint means for securing the knee of a user relative to said knee exercise assembly during exercise of the knee.

2. An apparatus according to claim 1 wherein said first resistance means comprises a hydraulic rotary actuator operatively connected to said knee exercise assembly.

3. An apparatus according to claim 1 wherein said second resistance means comprises a hydraulic rotary actuator operatively connected to said knee exercise assembly.

4. An apparatus according to claim 1 wherein said foot securement means is pivotably movable about two axes generally perpendicular to the horizontal axis about which said support member rotates, the first axis of movement corresponding to the said axis of tibial rotation movement of the knee and the second corresponding to an axis which is coaxial with the axis of abduction/adduction movement of the knee.

5. An apparatus according to claim 1 wherein said foot securement means includes a foot plate secured to said second resistance means and at least one strap element adjustably engaging the foot plate.

6. An apparatus according to claim 1 wherein said apparatus includes a seat for a user supported by said frame.

7. An apparatus according to claim 6 wherein said restraint means comprises a thigh restraint adjustably secured to said seat.

8. An apparatus according to claim 1 wherein said apparatus further includes restraint straps to immobilize the pelvis and trunk mounted to said frame.

9. An apparatus according to claim 1 comprising means to independently select the resistance to be provided by said first and second resistance means to flexion/extension movement and tibial rotation movement, respectively, of the knee of a user.

10. An apparatus according to claim 1 including first and second sensor means associated with said first and second resistance means, respectively, and an electrically associated computer for analyzing performance of the knee of the user during flexion/extension and tibial rotation movements, respectively.

* * * * *